(12) United States Patent
Hughes

(10) Patent No.: US 6,600,810 B1
(45) Date of Patent: Jul. 29, 2003

(54) MULTIPLE LAYER MULTILEAF COLLIMATOR DESIGN TO IMPROVE RESOLUTION AND REDUCE LEAKAGE

(75) Inventor: John H. Hughes, Martinez, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 09/131,177

(22) Filed: Aug. 10, 1998

(51) Int. Cl.$^7$ ................................................. G21K 1/04
(52) U.S. Cl. ..................................... 378/152; 378/147
(58) Field of Search ..................... 378/65, 145, 147, 378/149, 150, 151, 152

(56) References Cited

U.S. PATENT DOCUMENTS

| | | | |
|---|---|---|---|
| 4,463,266 A | 7/1984 | Brahme | 250/505.1 |
| 4,987,309 A | * 1/1991 | Klasen et al. | 250/492.1 |
| 5,166,531 A | 11/1992 | Huntzinger | 250/505.1 |
| 5,297,037 A | * 3/1994 | Ifuku | 378/65 X |
| 5,591,983 A | 1/1997 | Yao | 250/505.1 |
| 5,619,042 A | 4/1997 | Hughes | 250/492.3 |
| 5,748,703 A | * 5/1998 | Cosman | 378/152 |

* cited by examiner

Primary Examiner—Robert H. Kim
Assistant Examiner—Hoon K. Song

(57) ABSTRACT

Aspects of a multiple layer multileaf collimator capable of improving resolution for coverage of a target during radiation therapy are described. A multiple layer multileaf collimator includes a first layer of multiple elongated radiation blocking leaves supported by a first frame for individual leaf positioning in a first direction. The multiple layer multileaf collimator further includes a to second layer of multiple elongated radiation blocking leaves supported by a second frame for individual leaf positioning in a second direction, the second direction offset at a desired angle relative to the first direction, wherein the individual leaves of the first and second layers conform more closely with a target shape to improve resolution. Further, the second layer is positioned above the first layer and provides leakage coverage for the multiple elongated radiation blocking leaves of the first layer. The multiple layer multileaf collimator is not limited to a single type of multileaf collimator and thus is suitable for use in a variety of multileaf collimator designs, including single focus and double focus multileaf collimators.

17 Claims, 6 Drawing Sheets

MULTIPLE LAYER MULTILEAF COLLIMATOR DESIGN TO IMPROVE RESOLUTION AND REDUCE LEAKAGE

FIELD OF THE INVENTION

The present invention relates to collimators in radiation therapy devices, and more particularly to multiple layer multileaf collimator design to improve resolution and reduce leakage.

BACKGROUND OF THE INVENTION

During conventional radiation therapy treatment, a beam of radiation, varying in angles and intensities, is directed at an area of a patient, e.g., at a tumor. Typical treatment field shapes, square, rectangular, or a modification thereof, result in a three-dimensional treatment volume that, unfortunately, may include healthy tissue and organs. For obvious safety reasons, the dose capable of being delivered to the tumor is limited by the healthy tissue and organs in the path of the radiation beam. Since cure rates for many tumors are a sensitive function of the dose they receive, reducing the amount of exposed healthy tissue and organs is highly desirable in order to be able to increase the dose delivered to the tumor. Methods of making the treatment volume correspond more closely with a tumor include moving solid-jaw blocks during treatment, scanning the radiation beam over the volume to be treated, and using a multileaf collimator to create an irregularly shaped field related to the shape of the tumor.

An example of a multileaf collimator arrangement positioned about the central axis of a radiation-emitting head for shaping an irradiated beam is disclosed in U.S. Pat. No. 5,166,531, issued to Hunzinger on Nov. 24, 1992. Two opposing arrays of side-by-side elongated radiation blocking collimator leaves act in place of opposing solid jaw blocks. Each leaf in each opposing array can be moved longitudinally towards or away from the central axis of the beam, thus defining a desired shape through which the radiation beam will pass.

An enhancement on the multileaf collimator approach is described in U.S. Pat. No. 5,591,983, issued to Yao on Jan. 7, 1997. In Yao, a multiple layer multileaf collimator design is formed through first and second layers of a plurality of elongated radiation blocking leaves. The leaves of each layer are arranged adjacent one another so as to form two opposed rows of adjacently positioned leaves and are movable in a longitudinal direction which can be either generally transverse to or in the same direction of the beam. The layers are arranged one above another in the beam direction and offset in a lateral direction, so that spaces between adjacent leaves of the first and second layers are positioned over and under, respectively, leaves of the respective first and second layers. The arrangement of the leaves allows a reduction in problems of radiation leakage between leaves of a multileaf collimator. However, the arrangement does not provide as fine a resolution as desired to allow more accurate block positioning for creating a block volume in correspondence with a tumor shape.

Accordingly, what is needed is a system and method for utilizing a multiple layer multileaf collimator arrangement that improves resolution and reduces leakage for radiation delivery. The present invention addresses such a need.

SUMMARY OF THE INVENTION

The present invention provides aspects of a multiple layer multileaf collimator capable of improving resolution for coverage of a target during radiation therapy. A multiple layer multileaf collimator includes a first layer of multiple elongated radiation blocking leaves supported by a first frame for individual leaf positioning in a first direction. The multiple layer multileaf collimator further includes a second layer of multiple elongated radiation blocking leaves supported by a second frame for individual leaf positioning in a second direction, the second direction offset at a desired angle relative to the first direction, wherein the individual leaves of the first and second layers conform more closely with a target shape to improve resolution. Further, in a preferred aspect, the second layer is positioned above the first layer and provides leakage coverage for the multiple elongated radiation blocking leaves of the first layer.

Through the present invention, more precision in blocking radiation from healthy tissue and organs during radiation therapy is achieved. Such benefits are particularly significant to provide more effective treatment in the elimination of unhealthy target areas. Thus, the present invention allows one to increase the dose delivered while not exceeding healthy tissue constraints. These and other advantages of the aspects of the present invention will be more fully understood in conjunction with the following detailed description and accompanying drawings.

DETAILED DESCRIPTION OF THE INVENTION

The present invention relates to a multiple layer multileaf collimator with improved resolution. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
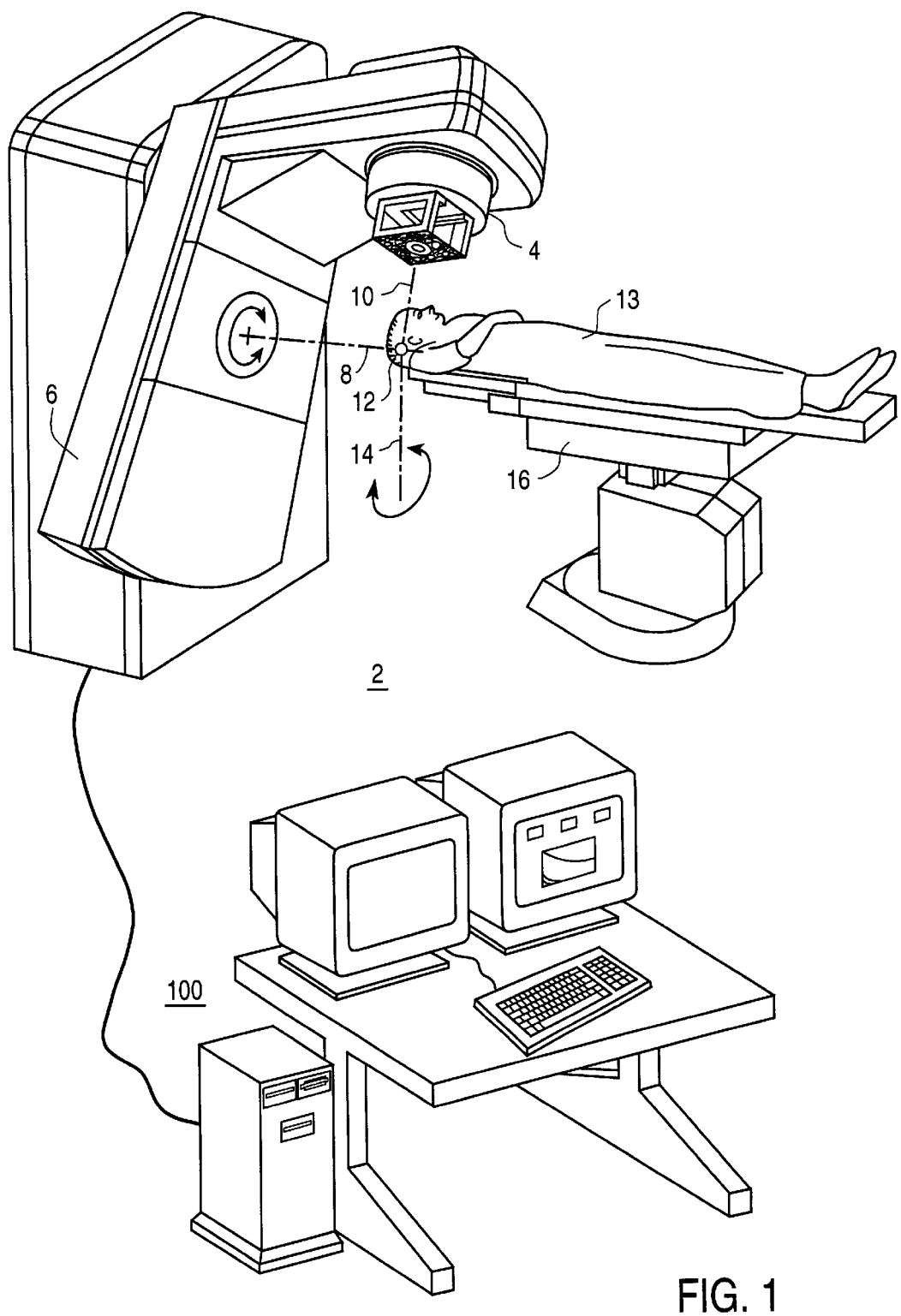
FIG. 1 illustrates a radiation treatment device including a multiple layer multileaf collimator in accordance with the present invention.

FIG. 1 illustrates a radiation treatment device 2 which utilizes a multiple layer multileaf collimator 4 in accordance with the present invention along with a treatment processing unit 100. The radiation treatment device 2 comprises a gantry 6 which can be swiveled around a horizontal axis of rotation 8 in the course of therapeutic treatment. Collimator 4 is fastened to a projection of gantry 6. To generate the high-powered radiation required for the therapy, a linear accelerator is located in gantry 6. The axis of the radiation bundle emitted from the linear accelerator and gantry 6 is designated 10. Electron, photon, or any other detectable radiation can be used for the therapy. During the treatment, the radiation beam is trained on a zone 12 of an object 13, for example, a patient who is to be treated, and who lies at the isocenter of the gantry rotation. The rotational axis 8 of the gantry 6, the rotational axis 14 of a treatment table 16, and the beam axis 10 all preferably intersect in the isocenter.

Figure 2A:
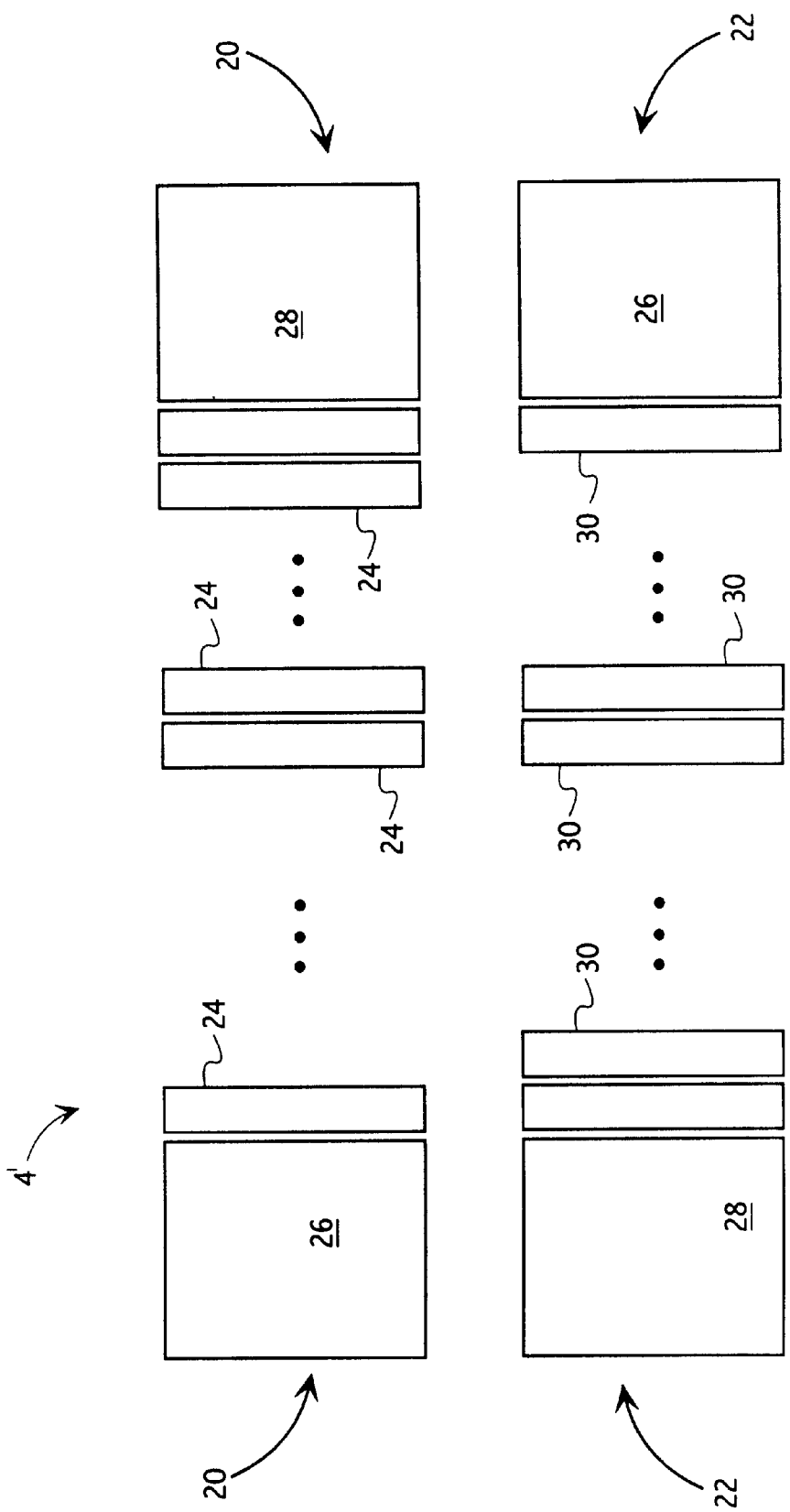
FIGS. 2a and 2b illustrate a multiple layer multileaf collimator arrangement of the prior art.

The multiple layer multileaf collimator 4 in accordance with the present invention suitably comprises two pairs of opposing elongated radiation blocking leaves, the pairs in separate planes and offset at a desired angle relative to one another. As mentioned above, a prior art approach to multiple multileaf collimator design is described in U.S. Pat. No. 5,591,983 (hereinafter Yao). FIG. 2a illustrates a side view of a prior art multiple layer collimator 4' as presented in Yao. Two identical layers, an upper layer 20 and a lower layer 22, of pairs of opposed leaves are shown. The top layer 20 comprises a middle section having a plurality of relatively narrow leaves 24 positioned in a side-by-side relationship, which is flanked on its left side by a relatively wide trimmer leaf 26 and on its right side by a relatively wide end leaf 28. The construction of bottom layer 22 is a mirror image of layer 20 and therefor common reference numbers are used for leaves 26 and 28. However, since in the middle section of layers 20 and 22, the narrow leaves are physically overlapping, the narrow leaves of layer 22 are referred by reference 30. It should also be noted that although wide and narrow leaves are shown in this embodiment, the leaves can all be of substantially the same widths or can be different widths and they could still be utilized within the spirit and scope of the present invention.

Figure 2B:
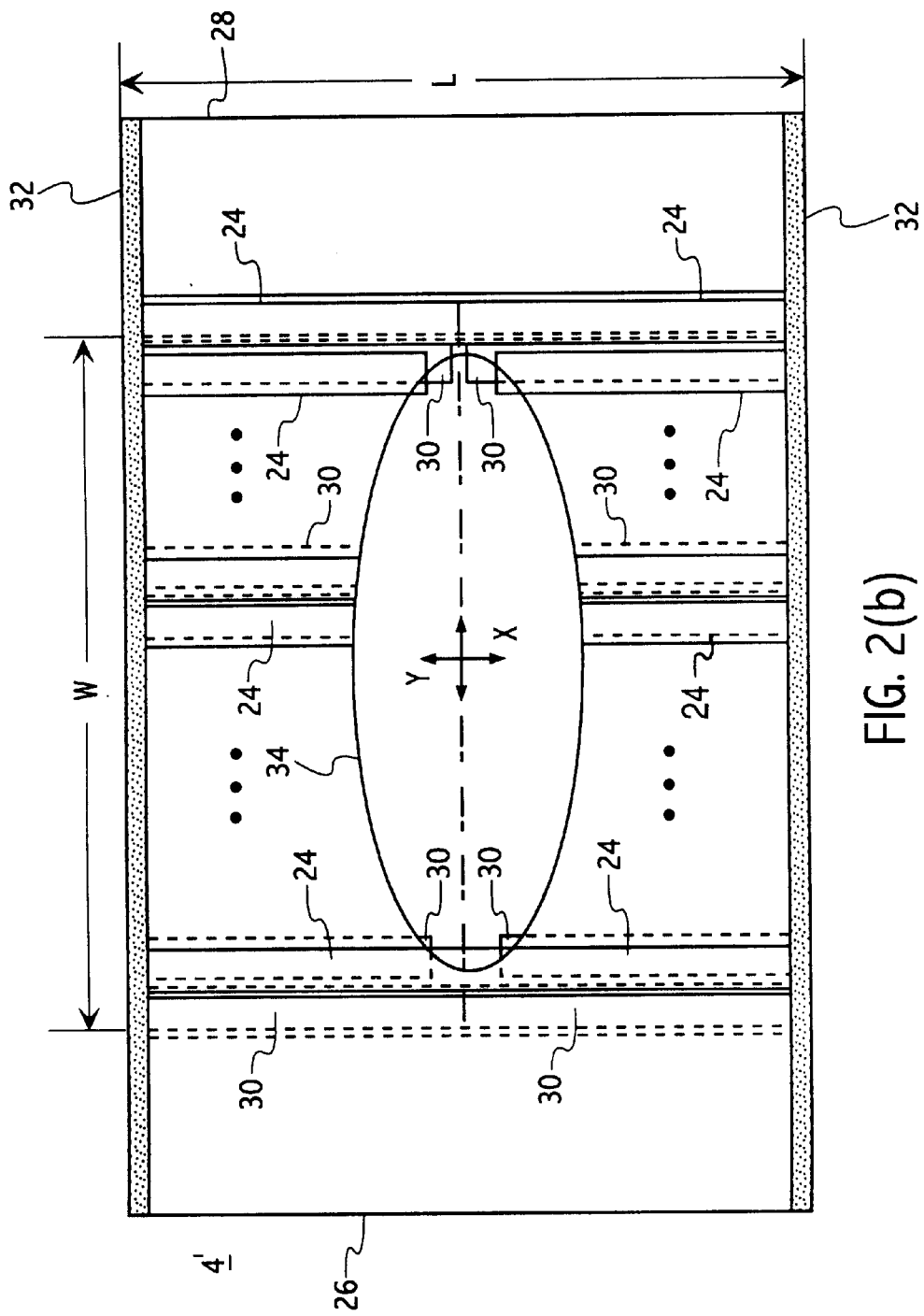

As shown in a top view of collimator 4' in FIG. 2b, top layer 20 being shown in solid lines and bottom layer 22 being shown in dashed lines, frame 32 supports each of the leaves 24 and 28 of the top layer 20 and each of leaves 30 and 28 of lower layer 22 in a paired opposed relationship, so that they are independently movable in their longitudinal dimension into and out of beam axis 10 (the Y direction shown in FIG. 2b). In general, the maximum size field is a rectangle of dimension W×L. For the illustration of FIG. 2b, the leaves 24 and 30 are shown in various positions to create shape 34. The operation of the leaves of layer 20 and layer 22 for creating a treatment field is as is conventional in prior art single layer multileaf collimator arrangements, which are well understood by those skilled in the art.

Figure 3:
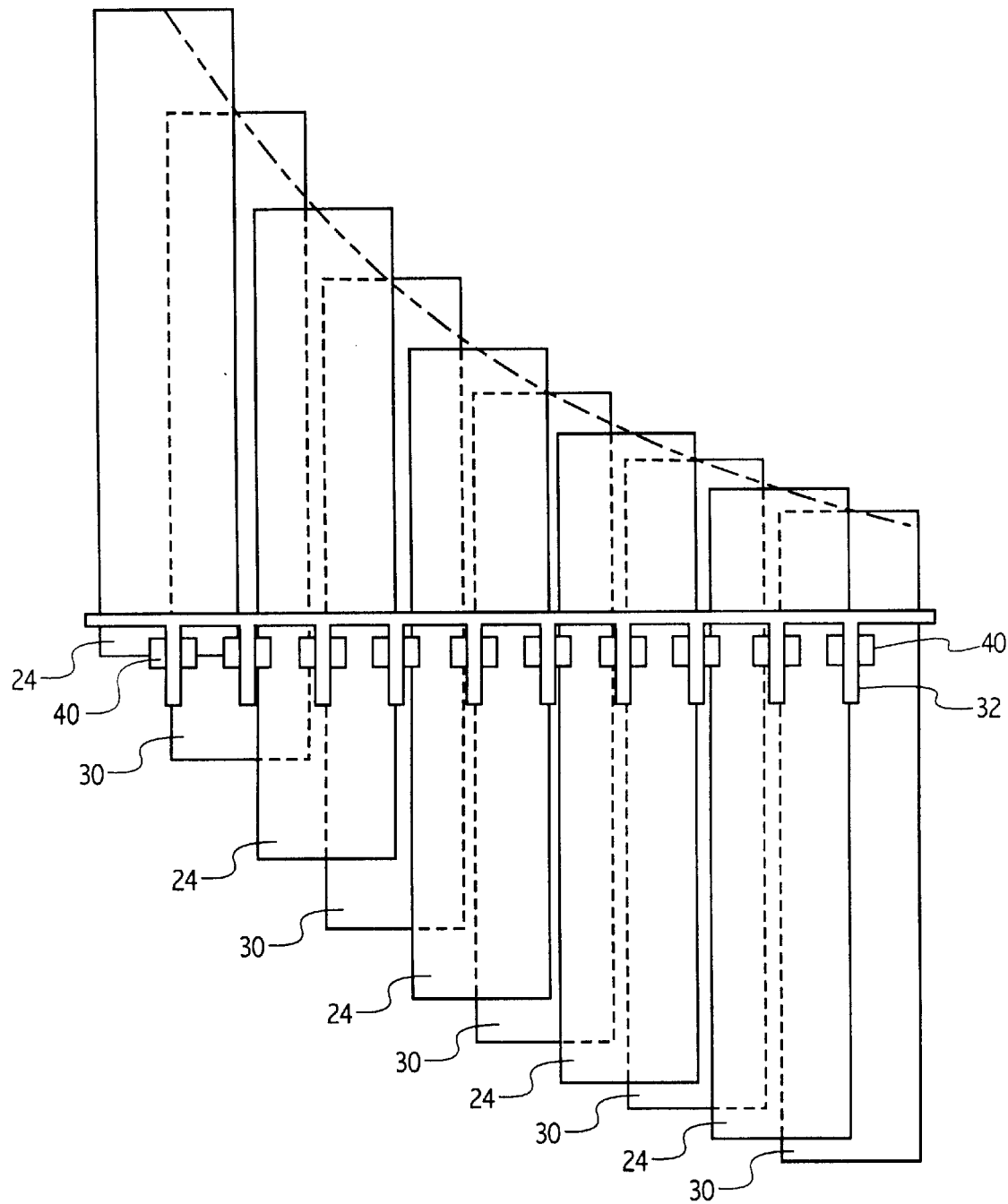
FIG. 3 illustrates a partial top view of the multileaf collimator arrangement of the prior art of FIG. 2b in greater detail.

FIG. 3 illustrates a portion of the top view of FIG. 2b in greater detail. As functionally shown therein, frame 32 includes a plurality of motors 40 mounted thereon which are used in a conventional manner to individually position the leaves, e.g, 24, and 30, of the collimator 4' into and out of the radiation beam for controllably defining the treatment field. One example of drive means (not shown) suitable for this is an individually driven worm gear for individually engaging a toothed track or floating nut mounted on each leaf. Details of one such prior art leaf driving means are provided in U.S. Pat. No. 5,160,847, issued to Leavitt, et al., on Nov. 3, 1992.

Figure 4:
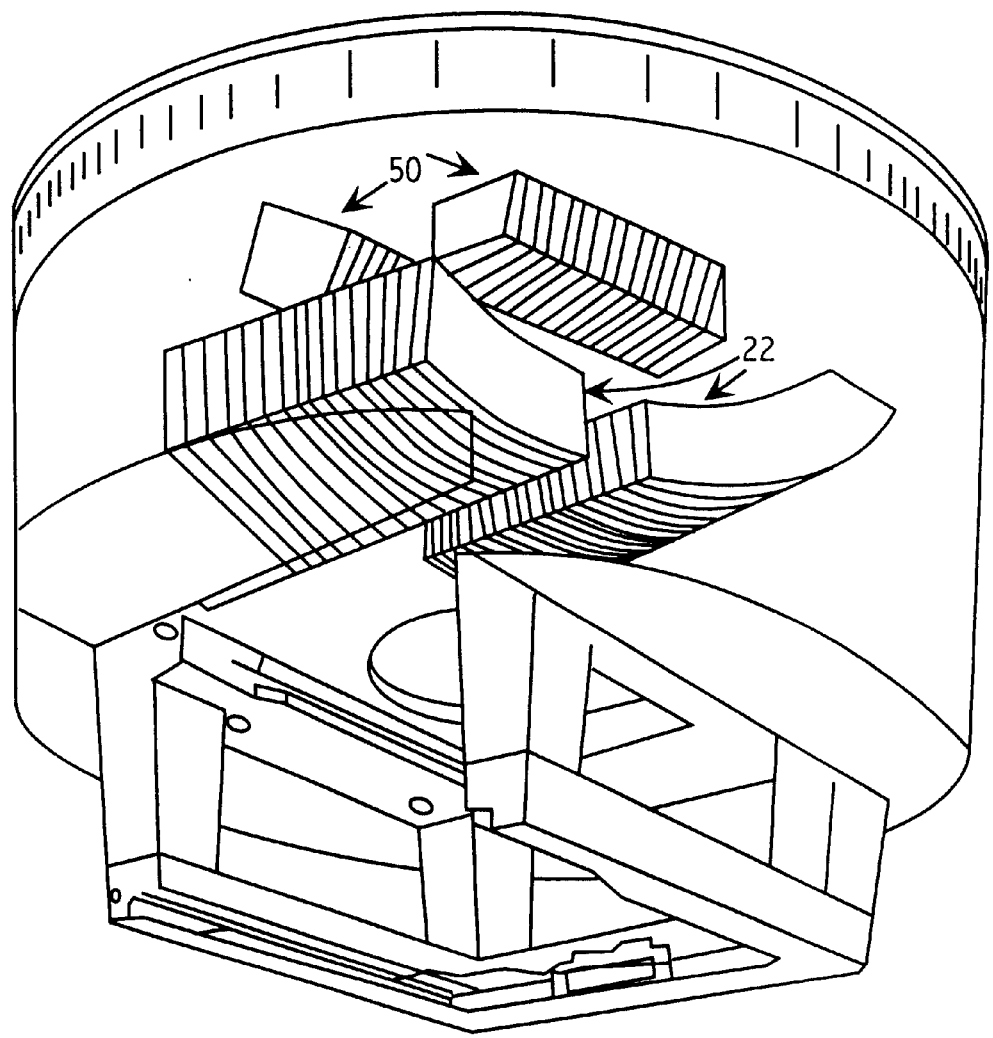
FIG. 4 illustrates a three-dimensional view of a multiple layer multileaf collimator in accordance with an embodiment of the present invention.

While providing a reduction in leakage through the arrangement of one layer over another and a shift of the blades in a lateral direction to cover gaps between blades in a lower layer, the prior art multiple layer multileaf collimator lacks preferred resolution in isolating the treatment area and avoiding undue exposure of healthy tissue or organs to the radiation therapy. The present invention improves resolution in a multiple layer multileaf collimator by providing a multiple layer multileaf collimator 4 comprising two layers of opposing pairs of elongated radiation blocking leaves, where the layers are not linked and can be rotated to within a desired angle, e.g., approximately between 0° and 90°, of one another. In a preferred embodiment, a top layer is capably positioned substantially between about 0° and 90° relative to a bottom layer. FIG. 4 illustrates a three-dimensional view of two multileaf layers, 22 and 50, in accordance with a preferred embodiment of the present invention. For convenience of illustration, layer 22 is described as being provided in a manner equivalent to layer 22 of the prior art shown in FIG. 2a. As shown in the example configuration of FIG. 4, multileaf layer 50 is positioned to be substantially perpendicular to multileaf layer 22. Layer 50 suitably comprises a multileaf collimator that functions similarly to multileaf layer 22 as described above, however, the positioning of the multileaf layer 50 to a desired angle through a conventional motor/control mechanism (not shown) allows greater resolution of coverage for targets than typical sold block arrangements or even the parallel multiple multileaf arrangement of Yao. Further, it should be appreciated that while in the arrangement of Yao differing widths are used for the end and trimmer leafs as compared with the middle section leaves, this serves as one example of a suitable leaf set. Of course, the present invention is capably achieved with other leaf arrangements, including those having leaves of substantially equivalent widths.

Figure 5:
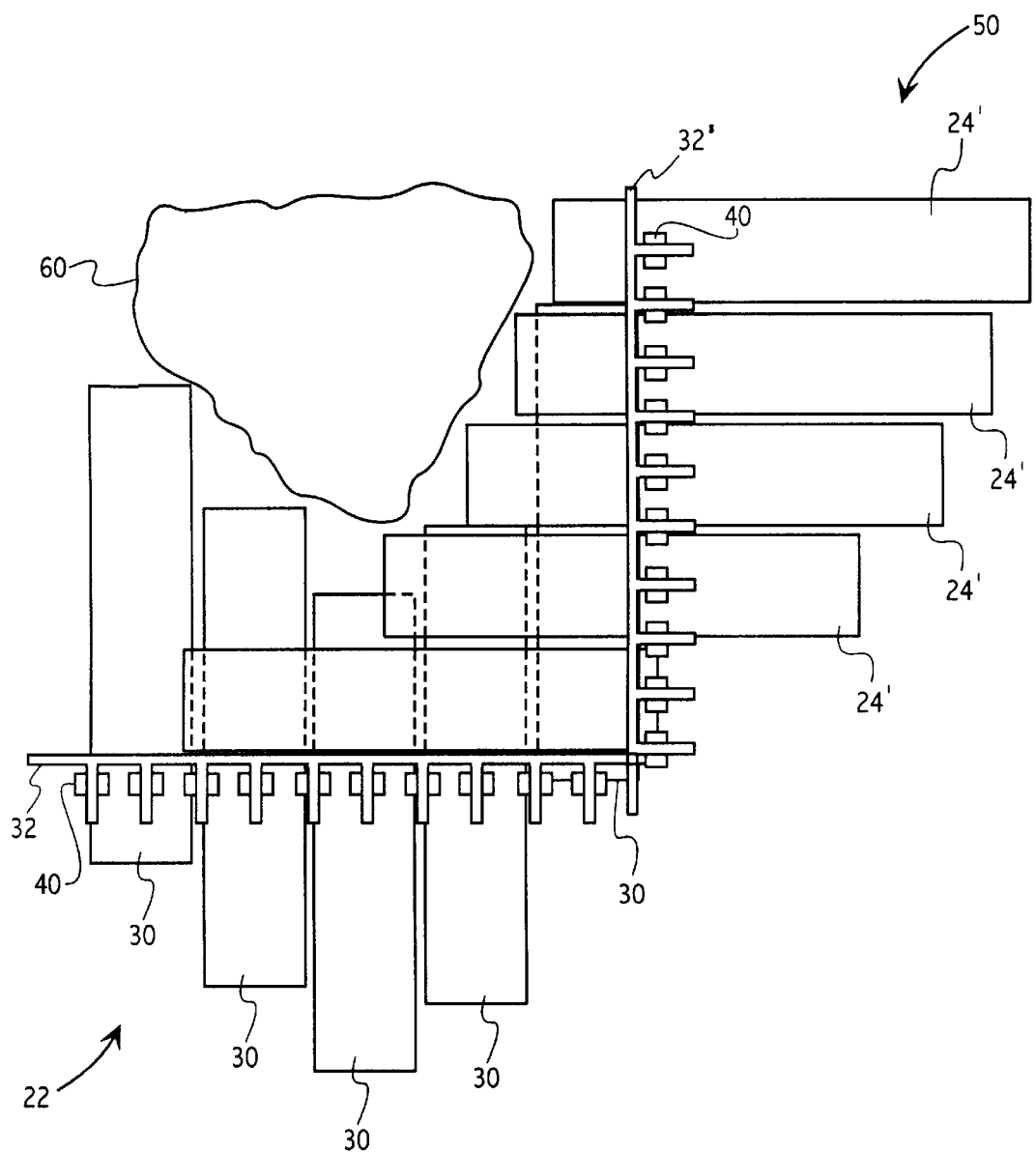
FIG. 5 illustrates a partial top view of the multiple layer multileaf collimator in accordance with the present invention.

FIG. 5 illustrates more particularly coverage capabilities for a multiple layer multileaf collimator arrangement in accordance with the present invention. In FIG. 5, a partial top view of one-half of each multileaf layer 22 and 50 is shown, where a top multileaf layer 50 is positioned at a preferred angle of about 90° (i.e., substantially perpendicular) relative to a bottom multileaf layer 22. As further shown in FIG. 5, the individual leaves of each layer, 30 in layer 22 and 24' in layer 50, are separately movable via motors 40 attached to frame means 32 and 32', respectively, operating as described above. The placement of multileaf layer 50 at an angular offset, e.g., of about 90°, allows the individual leaves 24' to be moved in close proximity to and in a close correspondence with a target 60, e.g., a tumor, from multiple directions rather than being limited to merely equivalent directions as in the layer arrangement of Yao. Thus, the resolution of coverage for targets is improved, as well as gaining the advantage that because there is crossing over between the top and bottom layer, the leakage areas between leaves are protected.

It should be appreciated that the multiple multileaf arrangement in accordance with the present invention is suitable for use with any type of multileaf design type or beam defining system, as is known and/or in use in the art. For example, the present invention is applicable in single focus and double focus multileaf collimators. An example of a single focus multileaf collimator is provided in the aforementioned U.S. Pat. No. 5,166,531, while an example of a double focus multileaf collimator is provided in U.S. Pat. No. 4,463,263 issued Jul. 31, 1984 to Brahme. Thus, the present invention is suitable with multileaf collimator designs that employ blades/leaves of varying thickness, size, depth, etc.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A multiple layer multileaf collimator capable of improving resolution for coverage of a target during radiation therapy, the multiple layer multileaf collimator comprising:
   a first layer of multiple elongated radiation blocking leaves supported by a first frame for individual leaf positioning in a first direction; and
   a second layer of multiple elongated radiation blocking leaves supported by a second frame for individual leaf positioning in a second direction, the second direction offset at a desired angle x, where $0° \leq x \leq 90°$, relative to the first direction to achieve an arrangement of the first layer and second layer that ranges from parallel to perpendicular through rotation of the second layer relative to the first layer, wherein the individual leaves of the first and second layers conform more closely with a target shape to improve resolution.

2. The multiple layer multileaf collimator of claim 1 wherein the second layer is positioned above the first layer.

3. The multiple layer multileaf collimator of claim 2 wherein the second layer provides leakage coverage for the multiple elongated radiation blocking leaves of the first layer.

4. The multiple layer multileaf collimator of claim 1 wherein the desired angle comprises an angle of about 90°.

5. The multiple layer multileaf collimator of claim 1 further comprising a plurality of motor means with the first and second frames for the individual leaf positioning of the first and second layers.

6. The multiple layer multileaf collimator of claim 1 wherein the first layer further comprises two opposing arrays of elongated radiation blocking leaves.

7. The multiple layer multileaf collimator of claim 1 wherein the second layer further comprises two opposing arrays of elongated radiation blocking leaves.

8. A radiation emitting device with improved resolution coverage for a target during radiation therapy, the radiation emitting device comprising:
   a radiation source for providing a radiation beam; and
   a collimator for shaping the radiation beam, the collimator comprising a first layer of multiple elongated radiation blocking leaves supported by a first frame for individual leaf positioning in a first direction, and a second layer of multiple elongated radiation blocking leaves supported by a second frame for individual leaf positioning in a second direction, the second direction offset at a desired angle x, where $0° \leq x \leq 90°$, relative to the first direction to achieve an arrangement of the first layer and second layer that ranges from parallel to perpendicular through rotation of the second layer relative to the first layer, wherein the individual leaves of the first and second layers conform more closely with a target shape to improve resolution.

9. The radiation emitting device of claim 8 wherein the second layer is positioned above the first layer.

10. The radiation emitting device of claim 9 wherein the second layer provides leakage coverage for the multiple elongated radiation blocking leaves of the first layer.

11. The radiation emitting device of claim 8 wherein the desired angle comprises an angle of about 90°.

12. The radiation emitting device of claim 8 further comprising a plurality of motor means with the first and second frames for the individual positioning of the multiple elongated radiation blocking leaves of the first and second layers.

13. The radiation emitting device of claim 8 wherein the first layer further comprises two opposing arrays of elongated radiation blocking leaves.

14. The radiation emitting device of claim 8 wherein the second layer further comprises two opposing arrays of elongated radiation blocking leaves.

15. A method for improving resolution of coverage of a target during radiation therapy by a radiation emitting device, the method comprising:
   providing a first pair of opposing multiple elongated radiation blocking leaves in a first plane within a collimator of the radiation emitting device; and
   providing a second pair of opposing multiple elongated radiation blocking leaves in a second plane within the collimator, the second pair being rotatable to within a desired angular offset relative to the first pair to achieve an arrangement of the first pair and second pair that ranges from parallel to perpendicular, wherein the first and second pairs more closely conform with a target shape while avoiding leakage between the multiple elongated radiation blocking leaves.

16. The method of claim 15 wherein the second pair is rotatable to within approximately 0° and 90° of the first pair.

17. The method of claim 15 wherein the first plane is below the second plane.

* * * * *